(12) United States Patent
Ghalavand

(10) Patent No.: US 9,773,427 B2
(45) Date of Patent: Sep. 26, 2017

(54) CALORIE BALANCE SYSTEM

(71) Applicant: Shahrokh Ghalavand, San Rafael, CA (US)

(72) Inventor: Shahrokh Ghalavand, San Rafael, CA (US)

(*) Notice: Subject to any disclaimer, the term of this patent is extended or adjusted under 35 U.S.C. 154(b) by 269 days.

(21) Appl. No.: 14/703,219

(22) Filed: May 4, 2015

(65) Prior Publication Data

US 2015/0325142 A1    Nov. 12, 2015

Related U.S. Application Data

(60) Provisional application No. 61/990,922, filed on May 9, 2014.

(51) Int. Cl.
  *G09B 19/00* (2006.01)
  *G06F 19/00* (2011.01)

(52) U.S. Cl.
  CPC ..... *G09B 19/0092* (2013.01); *G06F 19/3475* (2013.01)

(58) Field of Classification Search
  CPC .............. G09B 19/002; G06F 19/3475; G01G 19/4146; A47G 21/02; A61B 5/1118; A61B 5/4866
  USPC ........................................................ 434/127
  See application file for complete search history.

(56) References Cited

U.S. PATENT DOCUMENTS

2005/0011367 A1* 1/2005 Crow ................... A47G 21/02
                                                                99/342
2010/0240962 A1* 9/2010 Contant ................ A47G 21/02
                                                                600/300
2013/0157232 A1* 6/2013 Ehrenkranz ........ G01G 19/4146
                                                                434/127
2014/0349257 A1* 11/2014 Connor .................. A47G 21/02
                                                                434/127
2016/0372004 A1* 12/2016 Pathak ............... G09B 19/0092

OTHER PUBLICATIONS

Pham, Cuong, and Patrick Olivier. "Slice&dice: Recognizing food preparation activities using embedded accelerometers." European Conference on Ambient Intelligence. Springer Berlin Heidelberg, 2009.*

* cited by examiner

*Primary Examiner* — Robert J Utama
*Assistant Examiner* — Kristen Dragon
(74) *Attorney, Agent, or Firm* — Steven A. Nielsen; www.NielsenPatents.com

(57) ABSTRACT

A calorie balance system is designed for consumers who are interested in having a proper and adequate diet while monitoring daily activities. Disclosed embodiments enable consumers to be continuously aware of their caloric intake and to compare their caloric intake with current calories expended. Calories burned or expended may be measured by fitness tracking devices. Enabled utensils such as cups, spoons and forks are equipped with means of wireless communication, an accelerometer, a three axis slope meter sensor, a microcontroller, a scale, an analog to digital converter and a microcontroller. Enabled utensils measure the weight of food consumed are report to the consumer's personal electronic device. The system is further enabled by consumers talking to an enabled utensil to report the type of food being consumed. The reported food weight is mapped to the type of food consumed and relevant food data is displayed.

3 Claims, 5 Drawing Sheets

CALORIE BALANCE SYSTEM

CROSS-REFERENCE TO RELATED APPLICATIONS

This is a utility application based upon U.S. patent application Ser. No. 61/990,922 filed on May 9, 2014. This related application is incorporated herein by reference and made a part of this application. If any conflict arises between the disclosure of the invention in this utility application and that in the related provisional application, the disclosure in this utility application shall govern. Moreover, the inventor(s) incorporate herein by reference any and all patents, patent applications, and other documents hard copy or electronic, cited or referred to in this application.

BACKGROUND OF THE INVENTION (1) Field of the Invention

The invention generally relates to calorie monitoring systems. More particularly, the invention relates to means and methods of using food utensils, software, hardware, fitness monitors and other components to allow users to track their daily caloric balance.

(2) Brief Summary of the Invention

The present invention overcomes shortfalls in the related art by presenting an unobvious and unique combination and configuration of methods and components to integrate eating utensils with hardware and software components to allow consumers to continuously and contemporaneously monitor their consumption and expenditure of calories.

The invention overcomes shortfalls in the related art by using an unobvious combination of: communication systems, personal electronic devices such as smartphones, tablets, eating utensils equipped with such features as processors, Wi-Fi, Bluetooth, software, monitor/vibrators, scales, microphones, batteries and other components.

Disclosed embodiments include the use of eating utensils such as spoons, forks, chopsticks and cups integrated with various components that may include batteries or other power supplies, communication systems such as Bluetooth, software and firmware, motion detectors, accelerometers, microphones, speakers, vibrators, and fitness trackers. The eating utensils may communicate with a server and database system and/or may communicate and integrate with personal electronic devices such as a laptop, desk top computer, tablet or smartphone. In the best mode known to date, the eating utensils are not equipped with microphones and microphones are used by a consumer's personal electronic device, such as smartphone or tablet.

Disclosed embodiments, sometime called The Calorie Balance System are designed for consumers who are interested in having a proper and adequate diet while taking into account their daily activities. Disclosed embodiments enable consumers to be aware of their caloric intake at every moment and to compare their caloric intake with current calories burned. Calories burned or expended may be measured by fitness tracking devices. By use of smart phones or other electronic devices, a consumer may continuously track their caloric balance. Disclosed embodiments include applications and software to enable Android, Windows and Mac devices to interact with the utensils.

Disclosed embodiments inform a consumer of their need to adjust their consumption of calories and exercise to achieve a desired result. The system may produce ideal or goal numbers with respect to calories to consume and calories to burn, to achieve a desired result. Disclosed embodiments calculate provide advantages over the prior art by calculating cholesterol, fat, carbohydrate and protein values of food consumed.

Disclosed embodiments include machines to carry out a multi-step process that may include the following steps:

1. A utensil such as a spoon, fork or cup weighs the food or fluid placed upon the utensil. The measured data is then transmitted to a personal electronic device, fitness tracker or other implement. Accelerometers, angle sensors and other components measure movement, inertia and other factors to accurately measure the weight of food and the number of servings consumed.

2. A consumer enters the name of each food being consumed. This data entry occurs by voice command or direct entry into a personal electronic device. When a consumer changes the type of food being consumed, the consumer will then announce or otherwise enter the name of the new food being consumed. In the best mode known to date, a personal electronic device, such as a smart phone or table has a microphone and receives the verbal information from the consumer.

3. A microprocessor receives food type information from the consumer and then accesses a database to derive the attributes of the consumed food. Such food attributes may include calories, fat, protein, carbohydrates, and other variables. Accessed databases may be stored internally or external databases may be accessed via a network, such as the Internet.

4. Disclosed components, such as a microprocessor, machine readable instructions stored upon non-volatile memory calculates variables such as calories by factoring in the measured weights of food consumed and the types of foods consumed.

5. A fitness tracker or other similar consumer component may transmit a consumer's caloric output to the consumer's personal electronic device.

6. Disclosed components compare calories consumed and caloric output and inform the consumer of their caloric surplus or deficient. Armed with such information, a consumer may choose to adjust their caloric intake and/or caloric expenditures accordingly.

Typical consumer eating implements or utensils such as forks, spoons and cups are fitted with disclosed components and the disclosed components send data to the consumer's personal electronic device, such as a smartphone, watch, table or other implement. Data may be sent by any means. In the best mode known to date, data is sent via WiFi.

Disclosed embodiments may work using the following methodology:

A consumer may activate or turn on a disclosed eating implement such as fork, spoon or cup. An activated utensil may trigger the start of a computer implemented program residing upon the consumer's personal electronic device. A consumer may then use their voice to announce the food being consumed. The announcement is captured by the consumer's personal electronic device and using voice recognition, the properties of the announced food are obtained. A consumer may also manually enter the types of foods being consumed.

In a disclosed embodiment, the weight of the food is transmitted when the utensil reached a predetermined angle. In the best mode known to date, the optimal transmission angle is in the range of 15 to 35 degrees, with 25 degrees being the target. The use of a transmission angle assist in accurately weighing the served food, as the transmission angle has been found to coincide with a momentary stopping of movement. Such a moment of non-movement assists in the accurate weighting of the subject food as food inertia will not interfere with the weight measurement. During movement, a utensil will have difficulty accurately weighing food. With some consumers, their utensils are in almost constant action and stop only, and sometimes only briefly, when the food enters their mouth. The use of the transmission angle attempts to measure food weight at a time of minimal utensil movement. Disclosed utensils may also be equipped accelerometers to further discern moments of non-movement to attain accurate readings of food weight.

A microcontroller may command disclosed components and may be in communication with an ARP (amplifier) ADC (analogue to digital) converter. A reference voltage may be supplied to the microcontroller and used to weight of the food. In one disclosed embodiment, the amplifier's integrated circuit (IC) is NJM 4558 and the microcontroller may be an ATMEGA 32.

Disclosed embodiments may include an acceleration sensor. The output from the acceleration sensor may include a square wave, the square wave sometimes having a positive side being the same or mirroring the negative side. In a disclosed embodiment, the used acceleration sensor module comprises two acceleration waves for two axis (X, Y). If acceleration is zero the output wave for X or Y axis side was positive or negative acceleration. The positive side of the output square wave changed. For positive acceleration and for negative acceleration there is an increase in the positive side of the square wave. If we divide the positive side of the square wave to the negative side, we find the value of acceleration for the X or Y side. If the result from the division is less than one, the acceleration is positive and if the result is more than one the acceleration is negative.

Disclosed embodiments include a slope meter sensor attached to or integrated with a utensil. A slope meter sensor module may be connected to the microcontroller with SPI mode. A slope meter sensor may comprise a module with three registers that respond in response to changes in slope to the attached utensil. Disclosed embodiments include a slope meter sensor comprising means of measuring slopes on three axis X, Y and Z. For a point of reference the slope of Z axis is compared to the horizon. Measurements are enhanced by sampling angles over time. The slope meter sensor module may comprise or produce data in a three byte format, one for each axis of X, Y and Z.

Disclosed embodiments may comprise a WiFi module to transmit data from a utensil to a consumer's personal electronic device. The consumer's personal electronic device may act as a server. A WiFi module may comprise an input portal which may comprise a serial port. The WiFi module may accept data through the serial port, with the data coming from the micro controller. In one disclosed embodiment, a HLK module is used.

Different methods of sending data from a utensil to a consumer's personal electronic device are contemplated. The best method known to date is using WiFi due to easy conductivity with the typical smart phone.

As a utensil communicates with a consumer's personal electronic device, the consumer's personal electronic device may display data pertaining the food consumed.

These and other objects and advantages will be made apparent when considering the following detailed specification when taken in conjunction with the drawings.

REFERENCE NUMERALS IN THE DRAWINGS

Figure 1:
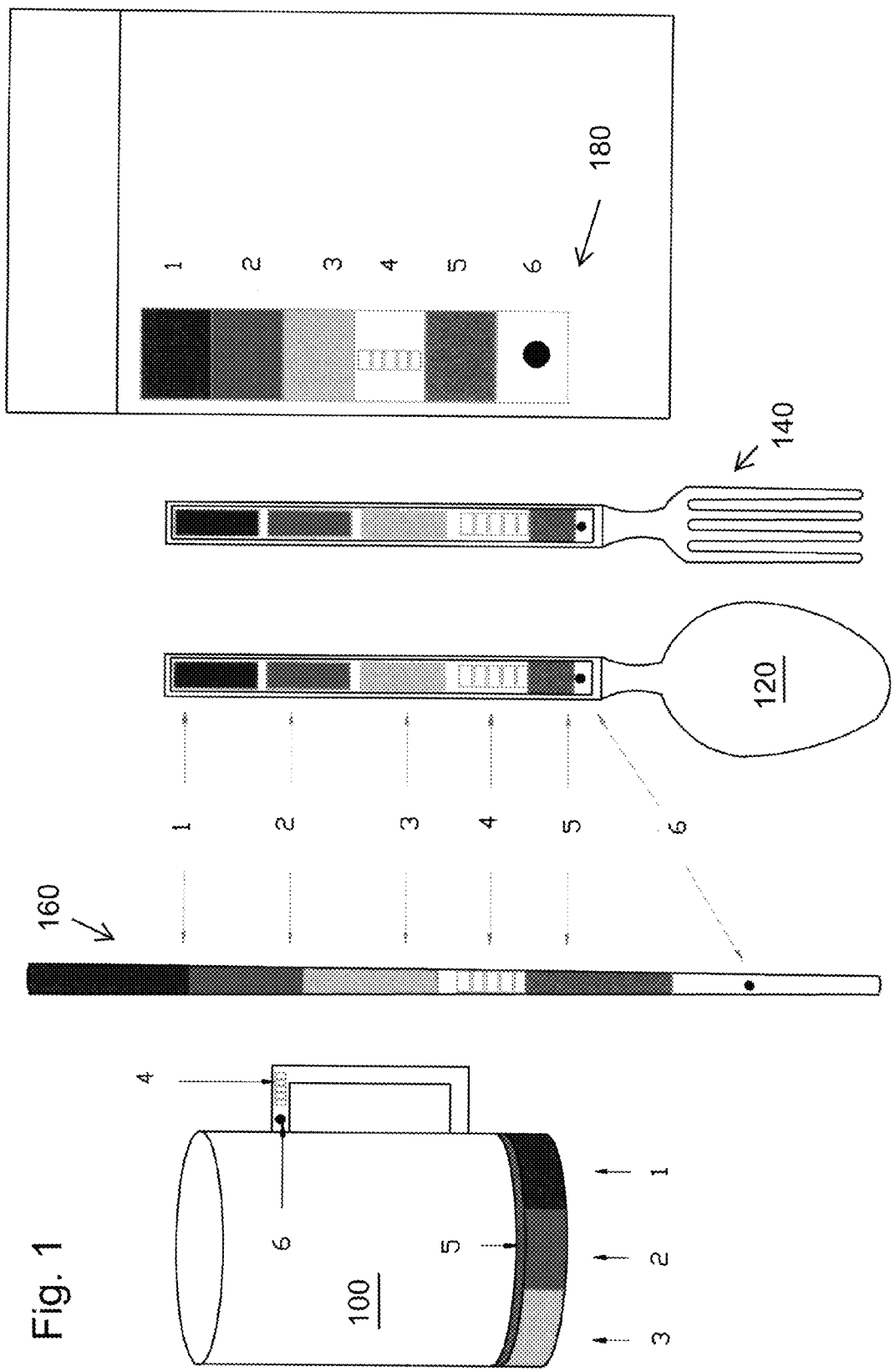
FIG. 1 depicts a schematic view of a contemplated system

A1 weight sensor within a spoon
A2 weight sensor within a fork
A3 weight sensor within a cup
B1 digital board within a spoon
B2 digital board within a fork
B3 digital board within a cup
D1 data from a spoon
D2 data from a fork
D3 data from a cup
D4 data from a fitness tracker
F food including liquids
H a horizontal plane
K kind of food declared by the consumer
R a range of angles wherein a utensil will send date
W weight of food placed upon a utensil
1 battery or other power supply
2 a WiFi system or other wireless communication system
3 software implementing the disclosed embodiments
4 a motion monitor such as an accelerometer and/or a vibrator
5 scale
6 microphone
100 cup
120 spoon
140 fork
160 chopstick
180 integrated module
200 fitness tracker
300 smart phone, laptop, tablet, personal electronic device or other computer system

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein,"

"above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines FIG. 1 depicts a disclosed embodiment comprising a plurality of eating utensils integrated with various components that may include batteries, Bluetooth, software, a monitor/vibrator system, a scale, a microphone, an optional speaker system and other components.

An eating utensil may use a microphone to receive user information, such as food consumed or desired goals. But, in the best mode known to date, an eating utensil does not have a microphone. Food information may be spoken by a consumer and a microphone in the consumer's personal electronic device may accept the verbal information. An eating utensil may weigh food via an integrated scale. An integrated motion monitor or accelerometer may measure the movement of an eating utensil. An integrated vibrator may cause an eating utensil to vibrate and thus warn a consumer to stop eating, or at least check their current caloric balance.

FIG. 1 depicts a cup 100 comprising a battery 1, a communication system 2, such as WiFi, machine implemented instructions, 3 or software, an accelerometer and angle sensor 4 and scale 5 and a microphone 6. The microphone upon the utensil is optional. A chopstick 160, spoon 120 and fork 140 are shown with similar components. A utensil may comprise a integrated module that may comprise an accelerometer and angle sensor 4 and scale 5 and a microphone 6

Figure 2:
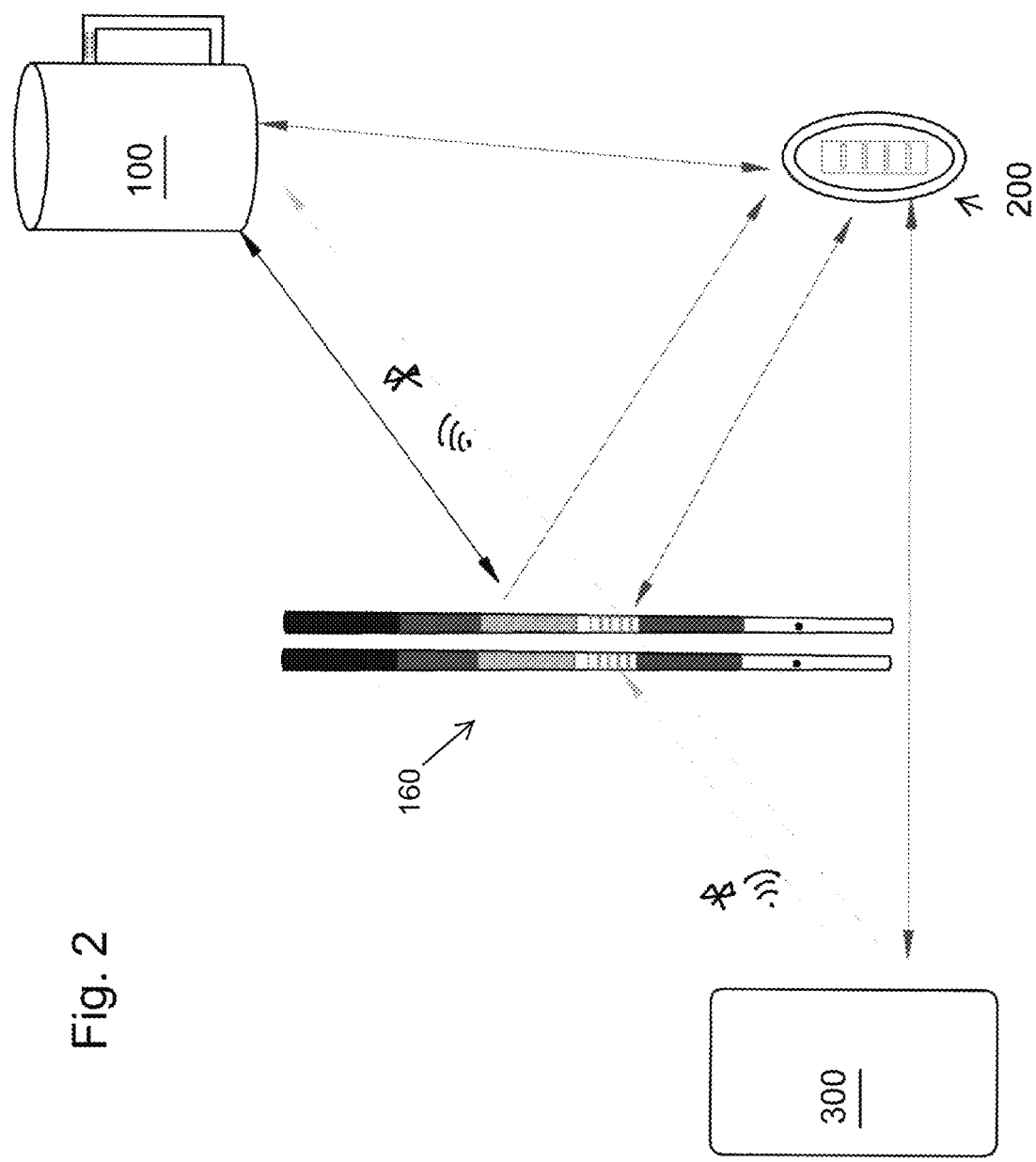
FIG. 2 depicts a disclosed embodiment in communication with a smart phone or other electronic device

FIG. 2 depicts eating utensils such as a pair of chopsticks 160 in communication with a fitness tracker 200 and a smart phone or other electronic device 300.

Figure 3:
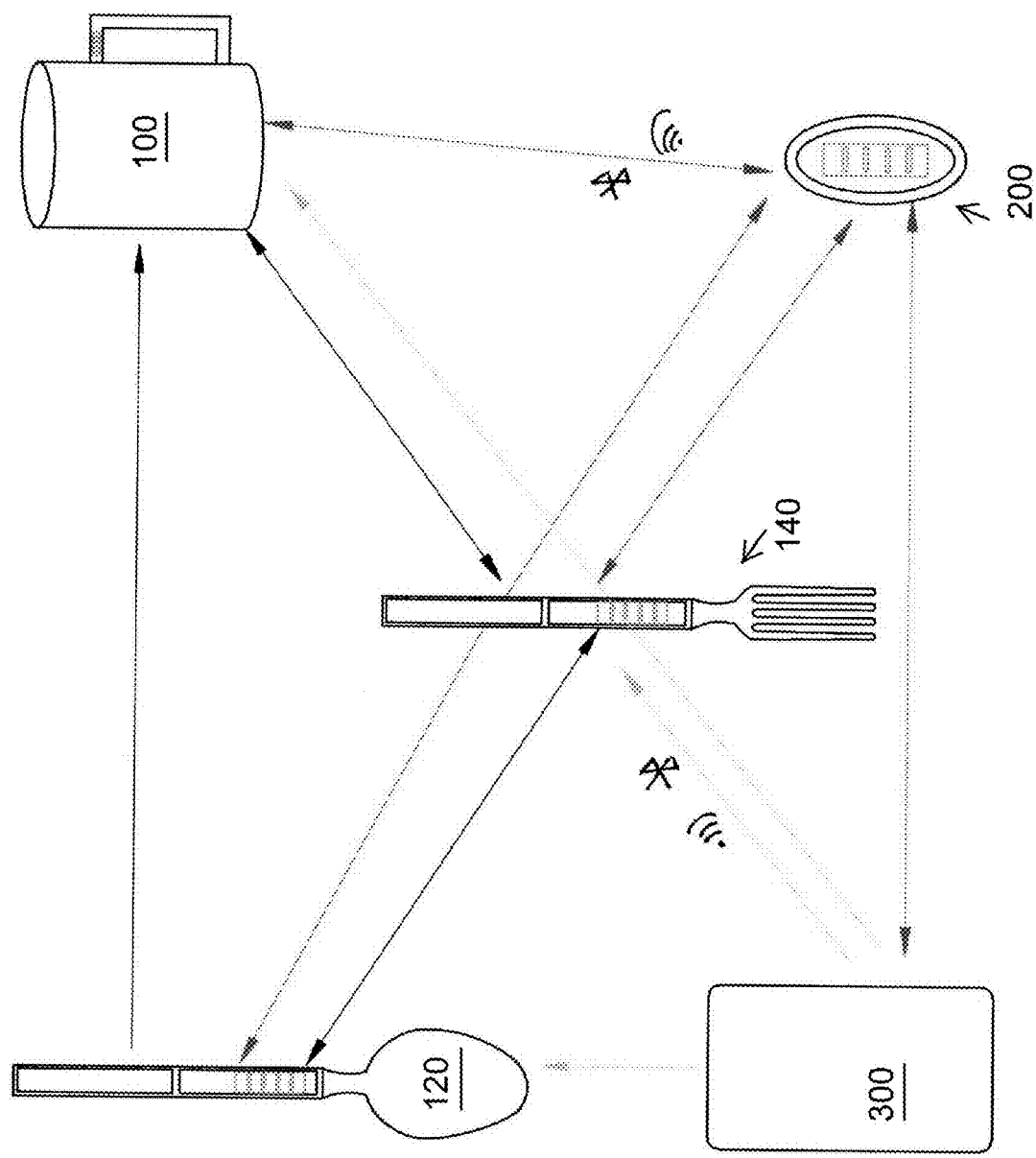
FIG. 3 depicts an integration of several eating utensils with the disclosed embodiments

FIG. 3 depicts a spoon 120, fork 140, cup 100, fitness tracker 200 and smart phone 300 in continuous communication.

Figure 4:
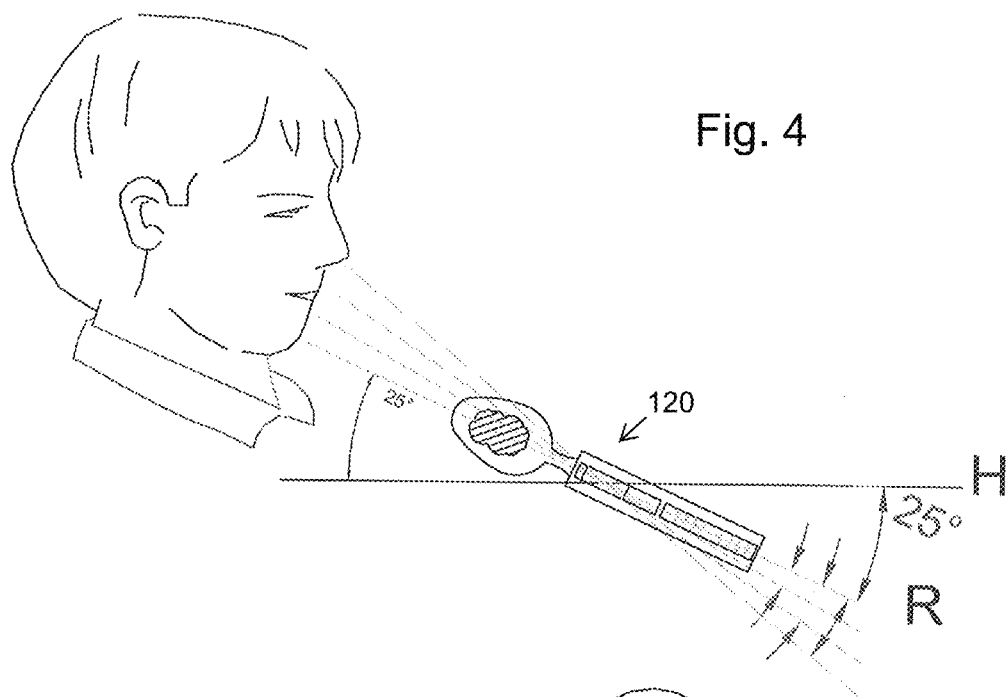
FIG. 4 depicts various elements of slope as used in disclosed embodiments

FIG. 4 depicts a consumer placing a spoon 120 at a range of angles R in the range of 15 to 35 degrees, with 25 degrees being the best mode known to date. Upon reaching the transmission angle R, the utensil will transmit food weight to the consumer's personal electronic device.

Figure 5:
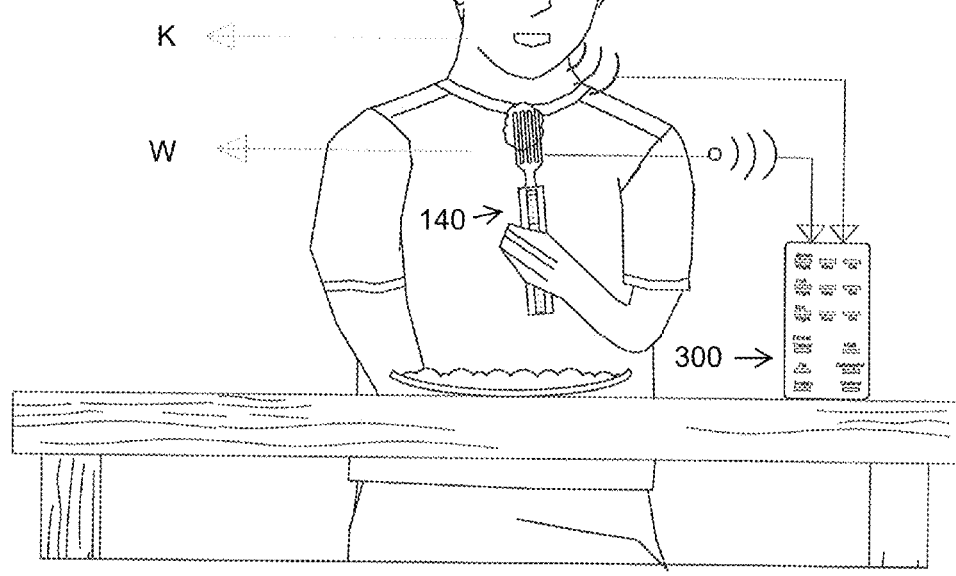
FIG. 5 depicts components of disclosed embodiments in communication with one another

FIG. 5 depicts a consumer stating the kind of food k being consumed. A microphone placed into a fork 140 accepts the voice input and transmits the input to the consumer's personal electronic device 300. The consumer's personal electronic device 300 may display the weight w of the food. The weight of the food is found by components integrated into the utensil. A consumer's personal electronic device 300 may include a display of calories consumed and other food related variables such as fat, protein, and carbohydrates. The display may also comprise a display of physical activity and calories expended. Disclosed embodiments include the use of applications and other software compatible with Android, Windows and Mac devices.

Figure 6:
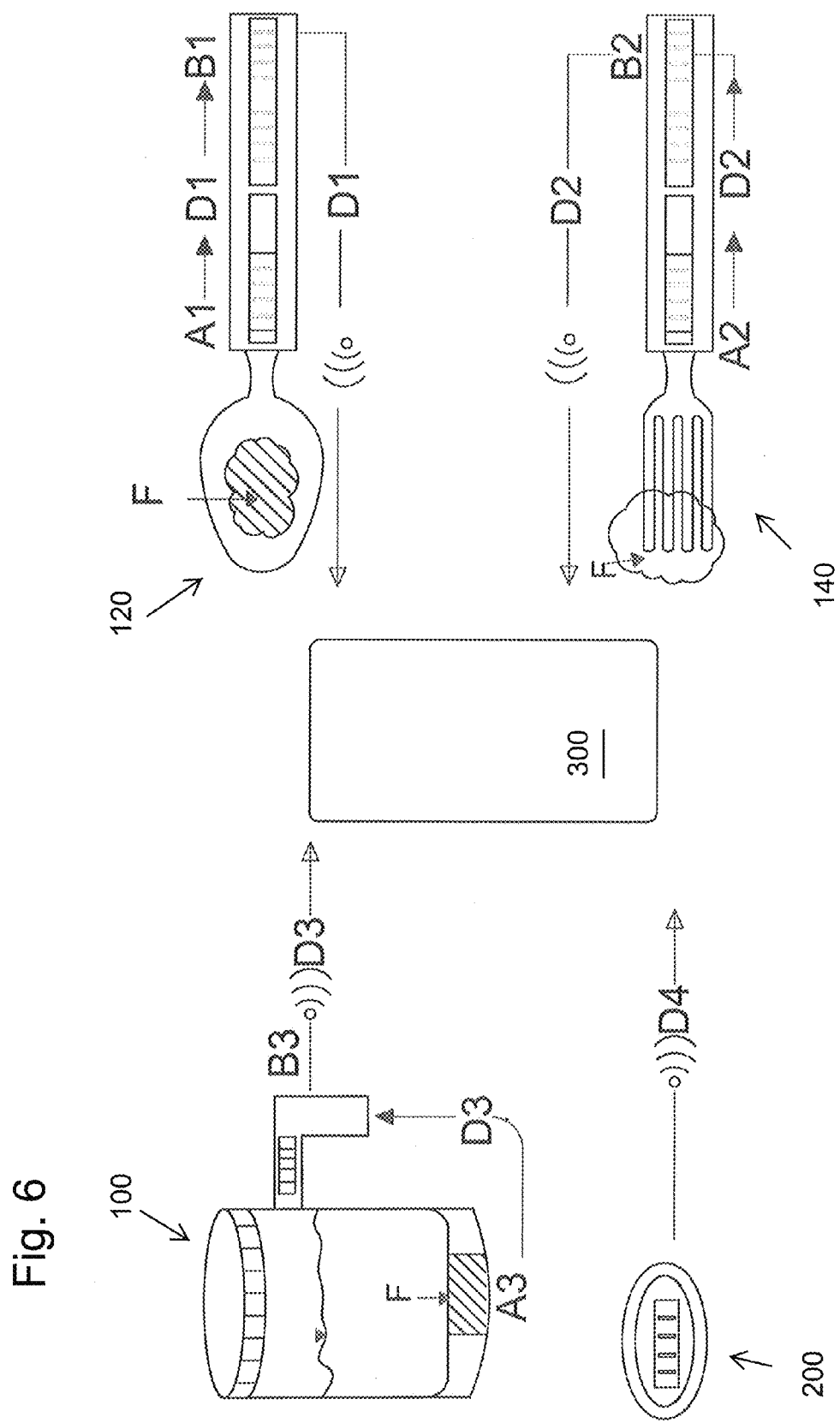
FIG. 6 depicts disclosed components in communication with a personal electronic device 100200

FIG. 6 depicts a cup 100 containing food F and the cup compromises a digital board B3, the digital board comprising a power supply, a wireless communication system, an accelerometer, a slope meter sensor, a microcontroller, a scale, an analogue to digital converter and a microphone. For the cup, the scale or weight sensor is shown as A3. Data from the cup D3 is transmitted from the scale A3 to the digital board B3. The digital board then transmits the data to the consumer's personal electronic device 300. The fork 140 and spoon 120 may operate in a similar fashion and be comprised of similar components.

Disclosed embodiments include the following items.

1. A system for measuring and reporting food intake, the system comprising:
   a) a utensil comprising an integrated module;
   b) the integrated module comprising a digital board comprising a power supply, a wireless communication system, an accelerometer, a slope meter sensor, a microcontroller, a scale and an analogue to digital converter;
   c) the integrated module further comprising machine readable instructions contained within the microcontroller;
   d) the integrated module in communication with a personal electronic device, the personal electronic device containing machine readable instructions to accept input from the integrated module and to produce a screen display showing calories consumed.

2. The system of 1 wherein the machine readable instructions of the integrated module sending a food weight measurement to the personal electronic device upon the utensil reaching an angle of between 15 to 35 degrees.

3. The system of 2 wherein the slope meter sensor comprises sensors upon an X axis, a Y axis and a Z axis.

4. The system of 3 wherein the machine readable instructions trigger a weight measurement upon the utensil reaching an angle of 15 to 35 degrees and upon the accelerometer having a reading of zero.

5. The system of 4 further including a fitness tracker in communication with the personal electronic device, the fitness tracker comprising an accelerometer and wireless communication system.

6. The system of 5 wherein the personal electronic device includes a database of food variables, the food variables comprising calories, protein, fat and carbohydrates.

What is claimed is:

1. A system for measuring and reporting food intake, the system comprising:
   a) a plurality of utensils each comprising an integrated module;
   b) the integrated module comprising a microphone, a digital board, the digital board comprising a battery or other power supply, a Wi-Fi system or wireless communication system, non-transitory medium containing an implementation software, an amplifier, an accelerometer, a slope meter sensor, a microcontroller, a scale and an analogue to digital converter;

c) the integrated module further comprising machine readable instructions contained within the microcontroller;

d) the microphone to receive voice input from a user, the received voice input from the user mapped to the type of food consumed by the user to create food data, the food data displayed upon a screen display, the screen display found upon a personal electronic device, the analogue to digital converter to convert the received input from the user, the scale to measure weight of the food consumed and the implementation software to implement this process of receiving, converting signal, weighing, and transmitting through Wi-Fi or wireless communication system;

e) the microcontroller in communication with the amplifier and the analogue to digital converter, the microcontroller to supply reference voltage to measure the weight of food being consumed;

f) the integrated module in communication with a the personal electronic device, the personal electronic device containing machine readable instructions to accept input from the integrated module and to produce a screen display showing calories consumed;

g) the machine readable instructions of the integrated module trigger a food weight measurement upon the utensil reaching an angle of 15 to 35 degrees and upon the accelerometer having a reading of zero and sending the food weight measurement to the personal electronic device; and h) the slope meter sensors in communication with the accelerometer, the slope meter sensors sense changes in slopes of the utensil on X, Y, and Z axes.

2. The system of claim 1 including wherein a fitness tracker in communication with the personal electronic device, the fitness tracker comprising an accelerometer and wireless communication system, the fitness tracker to receive input from personal electronic device through the wireless communication system, the fitness tracker to track burnt calories and to alert the user on the consumed calories.

3. The system of claim 2 wherein the personal electronic device includes a database of food variables, the database capable of adding new food variables, and the food variables comprising calories, protein, fat and carbohydrates.

* * * * *